United States Patent [19]

Carson, Jr. et al.

[11] Patent Number: 5,116,317
[45] Date of Patent: May 26, 1992

[54] ANGIOPLASTY CATHETER WITH INTEGRAL FIBER OPTIC ASSEMBLY

[75] Inventors: Richard F. Carson, Jr., Mission Viejo; Ronald J. Ehmsen, Villa Park, both of Calif.

[73] Assignee: Optimed Technologies, Inc., Orange, Calif.

[21] Appl. No.: 715,716

[22] Filed: Jun. 18, 1991

Related U.S. Application Data

[63] Continuation of Ser. No. 587,622, Sep. 19, 1990, abandoned, which is a continuation of Ser. No. 207,726, Jun. 16, 1988, abandoned.

[51] Int. Cl.$^5$ .................. A61B 1/06; A61M 29/00
[52] U.S. Cl. .................. 604/96; 606/191; 128/6
[58] Field of Search ............... 606/7, 191, 194; 604/96-101; 128/4-6; 65/3.12

[56] References Cited

U.S. PATENT DOCUMENTS

| | | |
|---|---|---|
| 3,498,286 | 3/1970 | Polanyi et al. |
| 3,866,599 | 2/1975 | Johnson. |
| 4,397,524 | 8/1983 | Yoshimura et al. |
| 4,418,688 | 12/1983 | Loeb. |
| 4,445,892 | 5/1984 | Hussein et al. |
| 4,448,188 | 5/1984 | Loeb ............................ 606/7 |
| 4,456,000 | 6/1984 | Schjeldahl ................... 128/344 |
| 4,470,407 | 9/1984 | Hussein ........................ 128/6 |
| 4,569,335 | 2/1986 | Tsuno. |
| 4,576,145 | 3/1986 | Tsuno et al. |
| 4,576,146 | 3/1986 | Kawazoe et al. |
| 4,619,247 | 10/1986 | Inoue et al. |
| 4,761,062 | 8/1988 | Loce et al. ................... 350/96.25 |
| 4,782,819 | 11/1988 | Adair. |
| 4,784,133 | 11/1988 | Mackin. |
| 4,790,295 | 12/1988 | Tashiro ......................... 127/6 |
| 4,892,099 | 1/1990 | Ohkawa et al. ............. 606/194 |

FOREIGN PATENT DOCUMENTS 0289021 11/1988 European Pat. Off.

OTHER PUBLICATIONS

European Search Report.
Pp. 1311-1314 of Article Entitled "In Vivo Coronary Angioscopy" by the American College of Cardiology.

Primary Examiner—C. Fred Rosenbaum
Assistant Examiner—William Lewis
Attorney, Agent, or Firm—Knobbe, Martens, Olson & Bear

[57] ABSTRACT

A balloon-type catheter is provided with an integral optical system utilizing illuminating fibers made of optical grade plastic, and an imaging bundle of many very small, flexible, fused glass fibers of pixels doped to increase the index of refraction and cladded together by doped glass with a much lower index of refraction than the pixels. A gradient index objective lens in the form of a cylinder of optical quality glass is attached to the distal end of the imaging fiber bundle. An inflation lumen is provided in the catheter for inflating the balloon, and a separate lumen conducts optically-transparent liquids to flush the field of view. The resulting catheter can be very small in diameter, is very flexible and is sufficiently inexpensive to be practically disposable.

8 Claims, 2 Drawing Sheets

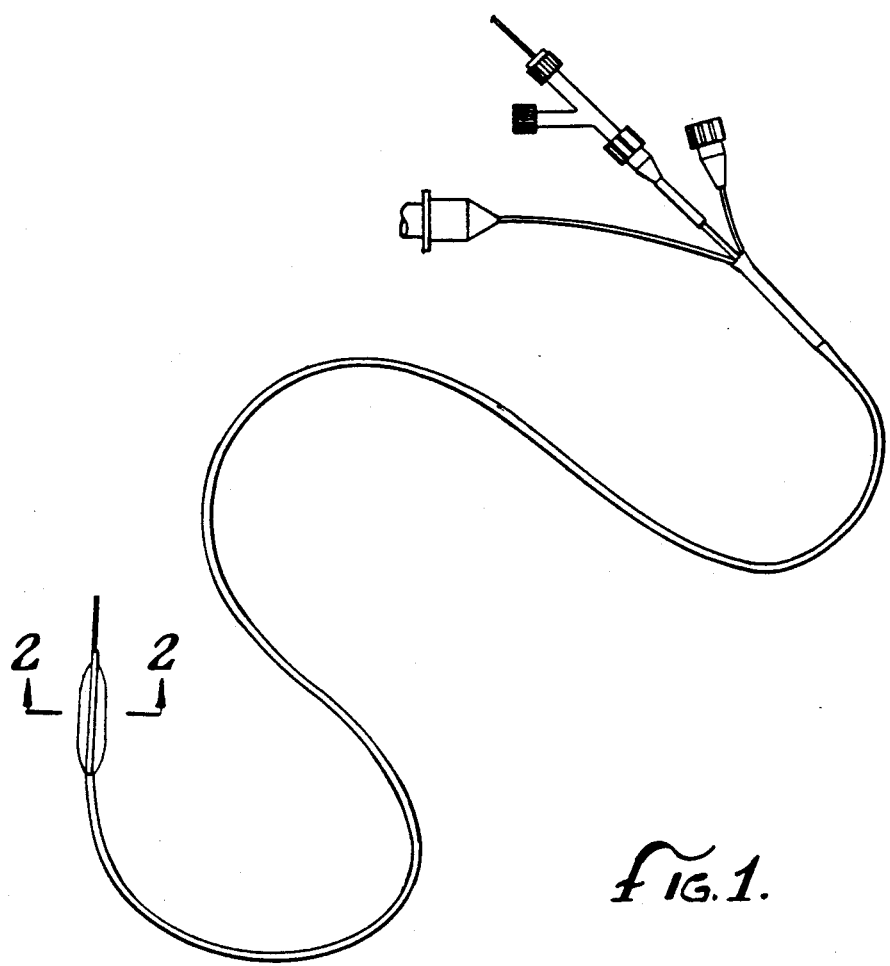
_fig.1._
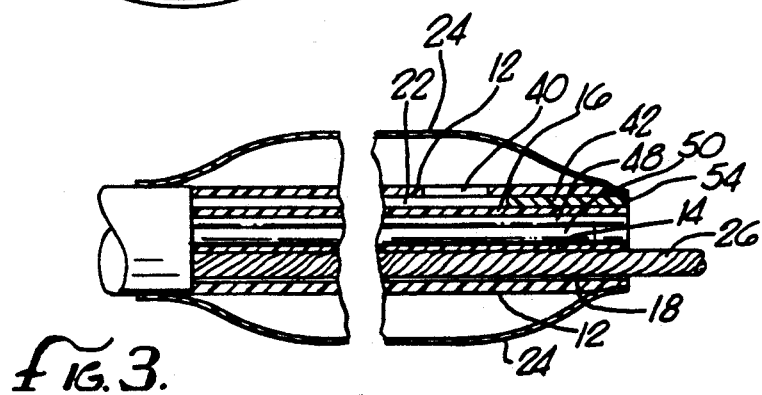
_fig.3._
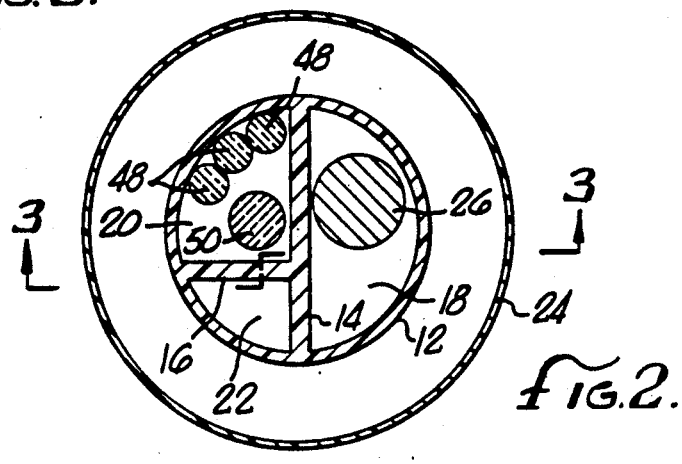
_fig.2._

ANGIOPLASTY CATHETER WITH INTEGRAL FIBER OPTIC ASSEMBLY

This is a continuation of application Ser. No. 07/587,622, filed Sep. 19, 1990, now abandoned, which is a continuation of Ser. No. 07/207,726, filed Jun. 16, 1988 for ANGIOPLASTY CATHETER WITH INTEGRAL FIBER OPTIC ASSEMBLY and now abandoned.

BACKGROUND OF THE INVENTION

This invention relates generally to the field of interventional medical catheters. More particularly, it relates to catheters used for coronary angioscopy and angioplasty, and similar medical procedures.

An increasingly common procedure for the treatment of atherosclerosis is the method known as Percutaneous Transluminal Coronary Angioplasty, or "PTCA." This procedure employs a long, flexible catheter having a tubular sheath with an internal fluid passage, and a radially expandable and contractible balloon coaxially surrounding the peripheral surface of the distal end of the catheter, in communication with the fluid passage. The catheter is inserted, via a guidewire, into a blood vessel (e.g., a coronary artery) having a localized stenosis, so that the balloon is located at the site of the stenosis. The balloon is inflated, with fluid injected into the passage, to dilate the vessel and relieve the stenosis.

Using this method, the location of the stenosis must first be determined by angiography, which yields only a shadowy, unclear image of the stenosis in one plane. Thus, it is difficult to determine the precise geometry and condition of the stenosis, and the proper positioning of the balloon is not readily confirmed. Consequently, the effectiveness of PTCA treatment is less than optimal, with a significant percentage of treated patients suffering a recurrence of the stenosis.

To overcome this problem, a class of instruments known as fiberscopes has been developed. A state-of-the-art fiberscope is disclosed in U.S. Pat. No. 4,576,145 to Tsuno, et al. The Tsuno, et al. device comprises an elongate flexible tube, the interior of which is divided by a plurality of longitudinally extending partitions into four longitudinal passages or lumens. A first lumen carries a plurality of optical fibers for transmitting illuminating light from an external source. A second lumen carries a light receiving or imaging, optical fiber. A third lumen is an inflation passage for an inflatable elastomeric balloon coaxially surrounding the tube near its distal end. The fourth lumen is for carrying a flushing liquid (such as saline solution) to an outlet at the distal tip of the tube.

A fiberscope of the type described in the Tsuno, et al. patent is used by inserting the distal end into a blood vessel, the interior of which is to be examined for, e.g., a stenosis. The balloon is then inflated with a fluid supplied by an injection device connected to the proximal end of the tube. The inflated balloon substantially reduces the flow rate of blood through the vessel, thereby allowing a relatively small volume of flushing liquid, ejected from the distal tip of the tube, to clear blood away from the area around the tube's tip. Light from the optical transmission fibers can then be used to illuminate this area, with the image of the area being conveyed to an observer by means of the imaging optical fiber.

While the above-described fiberscope provides a clear, detailed view of the area to be observed, the fiberscope must still be removed before most types of therapeutic procedures can be performed. It is possible, of course, to perform laser angioplasty by transmitting laser light through a suitable fiber optic assembly installed in one of the tube's lumens. Indeed, a number of prior art devices have contemplated this expedient, as exemplified in the following U.S. Pat. Nos.: 4,418,688 to Loeb; 4,445,892 to Hussein, et al.; and 4,448,188 to Loeb.

The prior art fiberscopes still suffer from a number of shortcomings. First, to achieve good visual resolution, relatively expensive optical components must be used, thereby making the overall unit too expensive to be disposable. This necessitates costly cleaning and sterilization for reuse. Second, the prior art devices are of a size (diameter) that makes them suitable for use only in larger blood vessels. Third, as previously mentioned, the prior art devices, except in some types of laser angioplasty, must be removed from the patient before therapeutic treatment of the stenosis is undertaken.

In an effort to overcome these disadvantages, there has been devised the concept of incorporating the features of a fiberscope into a balloon angioplasty catheter. This concept is disclosed in European Patent Application No. 85 304962.5, published Apr. 9, 1986 as Publication No. 0177124 in the name of Sumitomo Electric Industries, Ltd. As described therein, this catheter comprises a flexible, tube-like sheath with an expandible angioplasty balloon coaxially surrounding its distal end. The sheath contains a longitudinally-extending light guide for conducting light to the distal end of the catheter, and an imaging optical fiber bundle with suitable imaging lenses at its distal end for transmitting an image from the distal end of the catheter to the proximal end. The interior of the sheath is also provided with an inflation passage for transmitting fluid to inflate the balloon and a flushing liquid passage for conducting a flushing liquid through the catheter and out of an orifice in its distal end.

The device described in the above-identified European Patent Application is disclosed as capable of functioning concurrently as an endoscope to locate and observe a stenosis and an angioplasty device for relieving the stenosis. Thus, this device overcomes some of the above-mentioned limitations of prior art fiberscopes, in that observation and treatment can be performed with one instrument inserted a single time.

Nevertheless, certain drawbacks still exist. Specifically, the above-described device still uses standard optical components (i.e., fiber optics and lenses) thereby necessitating high costs and the requirement of cleaning and sterilization for reuse. Also, although some size reduction is achievable with this design, further size reduction is still desirable.

Thus, there has been established a need for a combined fiberscope/angioplasty catheter that combines good optical qualities with sufficiently low cost so as to be disposable. Further, such a device should be capable of being made in sufficiently small diameters to be usable in smaller blood vessels than has heretofore been possible.

SUMMARY OF THE INVENTION

Broadly, the present invention is an improved balloon-type PTCA catheter with an integral fiber optic assembly, wherein the improvement comprises the use of novel optical components that yield enhanced visual resolution at a substantially lower cost than was previously available in the prior art.

More specifically, a balloon-type PTCA catheter, in accordance with the present invention, includes an elongate, flexible, tubular sheath, internally partitioned into three longitudinal lumens. The first lumen contains the imaging and illuminating fiber optics that include the improvement to be described below. The second lumen is an inflation passage for conducting an inflation fluid to the angioplasty balloon that coaxially surrounds the sheath near the distal end of the catheter. The third lumen, larger in cross-sectional area than the other two, serves principally as a conduit for a guidewire or other ancillary devices, and also as a channel for the passage of optically transparent liquids for flushing blood away from the field of view at the distal tip of the catheter. This third lumen can also be used for blood pressure monitoring and for the injection of dyes, drugs, etc.

The novel aspects of the fiber optic assembly are mainly directed to the construction of the imaging optics. Specifically, the imaging optics include an imaging fiber bundle comprising a very large number (e.g., approximately 2000 to 3000) of individual image fibers, or pixels, made of fused silica glass doped with germanium dioxide to increase the index of refraction. The pixels are relatively small, on the order of three to four microns in diameter. They are bound together by a fluorine-doped glass with a much lower index of refraction than the pixels, thereby increasing the numerical aperture of the fiber, as will be discussed below in the Detailed Description of the Invention. The imaging fiber bundle is coated with an opaque coating, e.g., an ultraviolet-cured acrylate epoxy, for structural strength and for shielding the pixels from ambient light.

With the construction described above, the imaging fiber bundle provides higher image contrast, better resolution, and greater light sensitivity than the imaging fiber optics used in prior art fiberscopes. Moreover, the resulting fiber bundle is highly flexible, and its diameter is very small relative to fiber optic bundles with comparable light-gathering abilities. Finally, the fibers of the present invention's imaging fiber bundle are substantially lower in cost than those used in prior art angioscopes.

Another novel aspect of the imaging optics that provides a substantial improvement over the prior art is the imaging lens that is attached to the distal end of the imaging fiber bundle. This imaging lens is a gradient index objective lens, comprising a cylinder of optical quality glass having a refractive index that decreases, gradually and continuously, in the radially outward direction. Such gradient index lenses are considerably less expensive than the conventional geometric lenses used in prior art angioscopes. The lens is attached to the distal end of the imaging fiber bundle by an optically transparent epoxy adhesive that has very high optical transmission throughout the visible spectrum, while also being biocompatible.

A further novel aspect of the present invention is that the illuminating optical fibers are made of an optical-grade plastic (e.g., polymethylmethacrylate). Such plastics offer several advantages over the glass fibers used in prior art angioscopes: (1) more efficient light gathering characteristics; (2) greater flexibility; (3) ease of manufacture; and (4) lower cost.

As will be better appreciated from the detailed description that follows, the present invention constitutes a versatile, cost-effective PTCA catheter that is capable both of clear visualization of the interior of a blood vessel (or other bodily passage or cavity) and of effective therapeutic treatment of the visualized condition by any number of means, including balloon and laser angioplasty. Furthermore, as compared to prior art devices of this class, the present invention offers enhanced optical capabilities, while allowing sufficiently low cost of manufacture to provide a disposable device.

BRIEF DESCRIPTION OF THE DRAWINGS

FIG. 1 is a plan view of a PTCA catheter in accordance with a preferred embodiment of the present invention;

FIG. 2 is a cross-sectional view of the distal end of the PTCA catheter of FIG. 1, taken along line 2—2 of FIG. 1;

FIG. 3 is a longitudinal sectionalized view of the distal end of the catheter of FIGS. 1 and 2, modified to show the relevant elements;

DETAILED DESCRIPTION OF THE INVENTION

Figure 5:
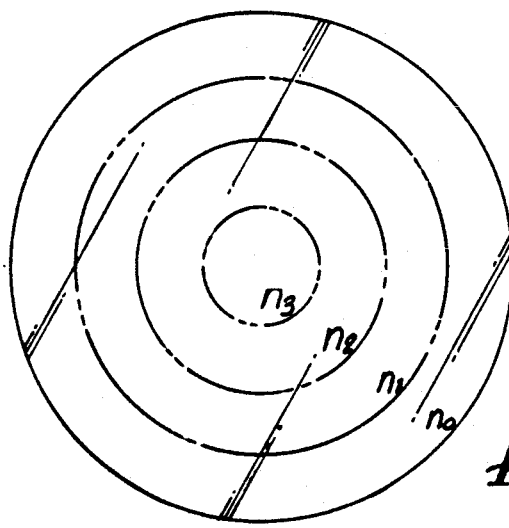
FIG. 5 is an end elevational view taken along line 5—5 of FIG. 4, showing the gradient index lens used in the present invention.

Referring now to the drawings, a PTCA catheter 10, in accordance with a preferred embodiment of the present invention, is described in detail.

The Catheter Assembly (FIGS. 1-3)

The catheter 10, as best shown in FIGS. 1, 2 and 3, includes an elongate, flexible tubular sheath 12, formed from a single extruded length of a suitable, biocompatible polymer. The interior of the sheath 12 contains first and second longitudinally-extending partitions, 14 and 16, respectively. The first partition 14 is substantially diametric, dividing the interior of the sheath approximately in half. The second partition 16 extends from the first partition 14 to the interior wall of the sheath and is located so as to divide its half of the interior of the sheath 12 into two longitudinal sections of unequal cross-sectional areas. Thus, the two partitions 14 and 16 divide the interior of the sheath 12 into three longitudinal sections, each of which may be of a different cross-sectional area. These sections define three longitudinal lumens: a large lumen 18, an intermediate-sized lumen 20 and a small lumen 22.

Attached to the distal end of the sheath 12, so as to surround its exterior surface coaxially, is an angioplasty balloon 24. The balloon 24 is made of a polymeric material (e.g., polyvinylchloride or polyethylene) that provides high strength, relatively low elasticity and relatively high rigidity upon inflation. Such angioplasty balloons are well-known in the art and need not be described in further detail herein.

Each of the three lumens mentioned above serves a different function. The large lumen 18 serves principally as a passage for the infusion of optically-transparent liquids to flush blood away from the field of view of the imaging optics of the catheter, as will be described below. Another important function of this large lumen 18 is to provide a passage for a guidewire 26 that is employed to guide the catheter 12 to the desired location within a blood vessel. The guidewire 26, which is shown in FIGS. 1, 2 and 3, does not need to be withdrawn from the lumen 18 after the catheter is in place. The large lumen 18 is large enough to provide a passage for infusion of radiopaque contrast fluids, thrombolytic drugs, etc. and, when the guidewire is removed, for introduction of various instruments, such as mechanical cutters, laser angioplasty fibers and blood pressure transducers.

For the purpose described above, the large lumen 18 has a distal opening 28 through which the fluids and/or the guidewire 26, or the instruments referred to above, emerge. The proximal end of the large lumen is connected, via a strain relief connection 30, to a first inlet tube 32, as shown in FIG. 1. The proximal end of the first inlet tube, in turn, is attachable to a Y-shaped inlet fitting 34, having a first branch 36 that serves as a liquid infusion port and a second branch 38 that serves as an entrance for the guidewire 26, or the other instruments, mentioned above, that can be passed through the large lumen 18.

The small lumen 22 serves as an inflation passage for the balloon 24. For this purpose, the small lumen has a peripheral orifice 40 passing through the wall of the sheath 12 and into the interior of the balloon 24. That part of the small lumen 22 between the orifice 40 and the distal end of the catheter is closed by a plug 42 or equivalent sealing means. The proximal end of the small lumen 22 is connected, via the strain relief connection 30, to a second inlet tube, or inflation tube 44. The proximal end of the inflation tube 44, in turn, is connected to an inflation port fitting 46, as shown in FIG. 1.

The intermediate-sized lumen 20 contains a plurality of illuminating optical fibers 48 and at least one imaging optical fiber bundle 50 with an imaging lens 52 at its distal end. These optical components will be described in detail below. The intermediate-sized lumen 20 runs the entire length of the sheath 12, the distal end of this lumen having an opening 54 at the distal end of the catheter (FIG. 3) and the proximal end terminating at the strain relief connection 30 (FIG. 1). The optical fibers 48 and 50 are carried from the strain relief connection 30 to an eyepiece 56 by means of a flexible, opaque conduit (tube 58). In some applications, the eyepiece can be replaced by an adaptor for coupling to a video camera (not shown). The eyepiece 56 also includes means (not shown) for transmitting light from a source (not shown) to the proximal ends of the illumination fibers 48. In some applications, tube 58 may consist of two separate conduits, one carrying the optical fibers 48 and the other carrying the optical fibers 50.

The Optical Components (FIGS. 2 and 4–8)

As mentioned above, the intermediate-sized lumen 20 contains the illuminating optical fibers 48 and the imaging optical fiber bundle 50. The illuminating optical fibers 48 are formed of an optical-quality transparent plastic, preferably polymethylmethacrylate or a suitable polymeric equivalent. Made of such a material, the illuminating fibers 48 offer several advantages over the glass fibers used in prior art angioscopes: (1) more efficient light-gathering characteristics; (2) greater flexibility; (3) ease of manufacture; and (4) lower cost.

Figure 7:
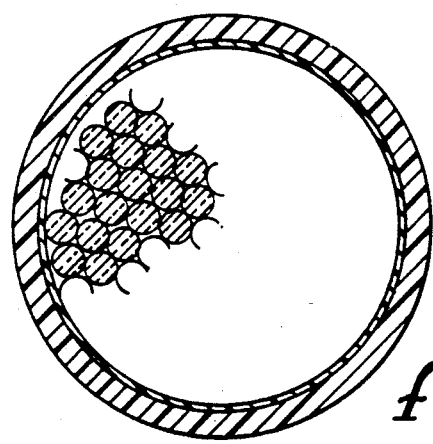
FIG. 7 is a cross-sectional view taken along line 7—7 of FIG. 6, showing some of the individual pixels that form the imaging fiber bundle of the present invention.
Figure 6:
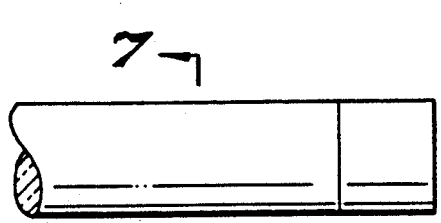
FIG. 6 is a side elevational view of the distal end of the imaging optics used in the present invention.
Figure 8:
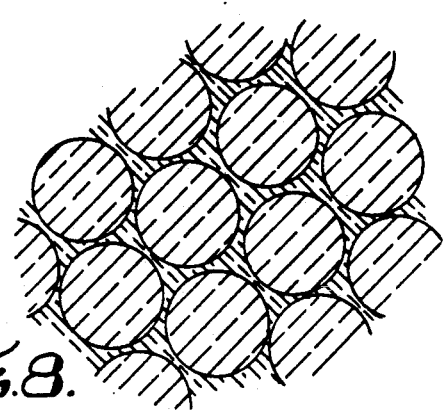
FIG. 8 is an enlarged, detailed view of a portion of the imaging fiber bundle shown in FIG. 7.

The imaging optical bundle 50, shown most clearly in FIGS. 6, 7 and 8, comprises a very large number of very small individual image fibers or pixels 60, only some of which are shown (not to scale) in the drawings. In a preferred embodiment of the invention, there are about 2000 to 3000 pixels, made of fused silica glass doped with germanium dioxide to increase the index of refraction. The pixels 60 are preferably about three to four microns in diameter and are bound together by a cladding 62 (FIG. 8), made of a glass doped with fluorine to lower its index of refraction, so that the cladding 62 has a much lower index of refraction than the pixels 60. The relationship between the indices of refraction of the pixels 60 and the surrounding cladding 62 provides an increased numerical aperture for the imaging fiber bundle, the significance of which will be discussed below. The bundle of pixels 60 is coated with an opaque plastic coating 64, preferably an ultraviolet-cured acrylate epoxy, for structural strength and flexibility and for shielding the pixels 60 from ambient light.

As mentioned above, the relationship of the pixel index of refraction to the cladding index of refraction yields a high "numerical aperture" (N.A.). The numerical aperture can be defined by the following equation:

$$N.A. = (n_p^2 - n_c^2)^{\frac{1}{2}} \qquad (1)$$

where $n_p$ is the pixel index of refraction, and $n_c$ is the cladding index of refraction. It can be seen that if the pixel index of refraction is much greater than the cladding index of refraction, the numerical aperture will be large.

The larger the numerical index, the more light that can be accepted by the imaging fiber bundle, and, therefore, the brighter the image. This is particularly important for intracardiovascular imaging, where it is desirable to minimize the amount of light necessary to illuminate the target and transmit the image. Since the imaging fiber bundle of the present invention can gather more light per unit area than the imaging fiber optics in prior art angioscopes, fewer illumination fibers (of the type described above) are needed. Moreover, "crosstalk" or the transmission of light from one pixel to another, is reduced, resulting in increased contrast as compared to prior art imaging optics. Still another advantage that obtains from the high light-gathering abilities of the above-described fiber bundle is that smaller pixels can be used. As mentioned above, pixels in the present invention can be from three to four microns in diameter, as compared to eight to ten microns in prior art devices. With smaller pixels, resolution is enhanced.

In the preferred embodiment of the invention, the pixel material is optimized for chromatic transmission, by techniques well-known in the art, to minimize color distortion.

The imaging fiber bundle, constructed in the manner described above, thus features improved optical characteristics, at lower cost, than prior art imaging fiber optics. Moreover, the resulting fiber bundle is highly flexible, having a bending radius as small as 30 mm on a sustained basis. This means that the bundle can be wrapped around a 30 mm mandrel with a weight suspended by the bundle, and the bundle does not fail or become damaged. In operation, the bundle can be satisfactorily bent through smaller radii. In addition, the improved optical characteristics of the fiber bundle allow its overall diameter to be substantially reduced, and because fewer imaging fibers are needed, the diameter of the entire catheter can be decreased, as compared to prior art fiberscopes.

Figure 4:
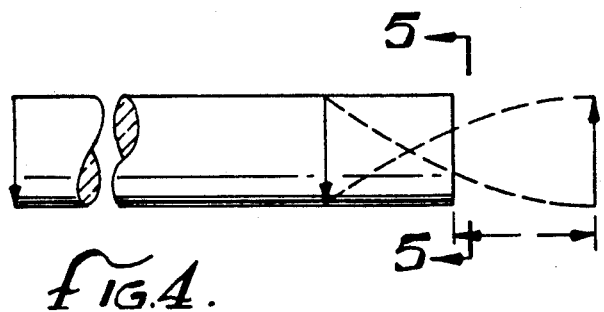
FIG. 4 is a partially diagrammatic side elevational view of the distal end of the imaging optics of the PTCA catheter of FIG. 1.

The imaging lens 52, shown most clearly in FIGS. 4, 5 and 6, is attached to the distal end of the imaging fiber bundle 50 by an optically transparent, biocompatible epoxy adhesive. A suitable epoxy adhesive is the one sold under the trademark EPO-TEX 301-2 by Epoxy Technology, Inc. of Billerica, Mass. This epoxy has an optical transmission of 98-99% from 0.31 to 2.5 microns, which includes the entire visible spectrum. It can be cured in 1½ hours at 80° C., and, when cured, has a Shore D hardness of 82, allowing it to be effectively polished.

The lens 52 itself is a gradient index objective lens, comprising a cylinder of optical quality glass having a refractive index that decreases, gradually and continuously, in the radially outward direction. Thus, referring to FIG. 5, which shows the end face of the lens 52, the highest index of refraction $n_3$ is at the center of the lens, with refractive indices $n_2$, $n_1$ and $n_0$ indicating progressively lower refractive indices at selected points along a radius 66 of the lens 52.

As shown in FIG. 4, the gradients index lens 52, is optically coupled to the image fiber bundle 50 so as to focus an inverted image 68 of an object 70 onto the distal end of the image fiber bundle 50, in a manner essentially equivalent to a conventional geometric lens. The inverted image 68 is then transmitted to the proximal end of the imaging fiber bundle, and from there to an optical receiver such as the eyepiece 56, where it is magnified and returned to its original orientation by suitable lenses (not shown). In a preferred embodiment of the invention, the lens 52 has a diameter of about 0.35 mm (slightly smaller than the inner diameter of the coating 64 of the imaging fiber bundle 50 as seen in FIG. 7). There is also a thin silica jacket 61 encasing the pixels 60. The lens 52 has a working distance, or focal length (in air), of approximately 5 mm, as indicated by the arrow 72 in FIG. 4. The "depth of field," however, is greater, ranging from about 2 to 10 mm.

The gradient index lens 52 offers optical qualities and performance similar to the conventional geometric lenses of prior art fiberscopes, but at considerably lower cost, especially in the very small sizes, the use of which is made possible by the present invention.

Use of the Invention

A PTCA catheter constructed in accordance with the present invention is inserted into a blood vessel (such as a coronary artery) by means of the guidewire 26. As the distal end approaches the suspected site of a stenosis, a transparent flushing liquid is passed through the large lumen 18 from the infusion port 36, emerging from the distal orifice 28 to clear blood away from the optical path of the illuminating and imaging optics. Visualization of the stenosis site is achieved by transmitting light through the illumination fibers 48, and then transmitting the illuminated image back to the eyepiece 56 by means of the lens 52 and the imaging fiber bundle 50.

When the balloon 24 is properly located with respect to the stenosis, it is inflated to relieve the stenosis by means of a suitable inflation fluid injected through the small lumen 22 and into the balloon 24 through the lumen orifice 40.

Alternatively, the balloon 24 can be inflated for the purpose of facilitating visualization, in the manner described above in connection with the description of U.S. Pat. No. 4,576,145 to Tsuno, et al. It is important to note that in small vessels, it generally will not be necessary to inflate the balloon for the purpose of occluding blood flow to facilitate visualization. When the balloon is employed for this purpose, it may be advantageous to inflate it only partially, since the purpose is only to reduce the blood flow through the vessel and not to exert pressure against its walls. When the catheter is used in this manner, the large lumen may be used for the passage of a variety of mechanical instruments to the desired location in the blood vessel, the guidewire 26 having been withdrawn. As previously mentioned, these instruments may include a laser for laser angioplasty, a micro-cutter, etc.

Thus, the present invention offers the physician the option of performing accurate angioscopy, along with a variety of other procedures. Of considerable importance is that both visualization (angioscopy) and treatment (angioplasty), can be performed with the same catheter. Thus, there is no need to insert and remove two different catheters, as was the common practiced with the prior art devices, as previously described.

Using the construction described above, the cost of the catheter can be minimized. This cost reduction is achieved mostly with the novel optical components of the present invention, which also achieves superior optical performance as compared to the prior art. As a result, the cost of the catheter is reduced sufficiently to allow the entire unit to be disposable, thereby eliminating the cleaning and resterilization required for the prior art angioscopy devices. Because the device is designed to be disposable, the illuminating fiber 48 and the imaging fiber bundle 50 are permanently fixed in the lumen 20 by a suitable biocompatible adhesive, such as an epoxy or polyurethane. This further reduces costs and increases structural strength, as compared to prior art devices, in which the optical components are removable from the sheath to facilitate cleaning.

Furthermore, as previously mentioned, the improved optical components in the present invention allow the overall diameter to be significantly reduced. For example, the outside diameter may be as small as 1.5 mm and, in a prototype, is about 1.45 mm. Such small sizes allow the present invention to be used in blood vessels that are significantly smaller than those that have been accessible with prior art devices.

All of the above-described advantages provide a PTCA catheter, in accordance with the present invention, that offers improved performance, greater versatility, increased cost-effectiveness, and improved convenience and ease of use, as compared to prior art devices of this general nature.

It will be appreciated that, while a preferred embodiment of the invention has been described herein, various modifications will suggest themselves to those skilled in the pertinent arts. For example, variations in the configuration of the invention may be devised to adapt the present invention for use in bodily passages or cavities other than blood vessels. The specific configuration of the lumens and their relative sizes may be modified to accommodate optical components of different sizes. These and other modifications that may suggest themselves to those skilled in the pertinent arts are considered to be within the spirit and scope of the present invention, as defined in the claims which follow.

What is claimed is:

1. A disposable angioplasty catheter comprising:
a flexible, tubular sheath with an inflatable balloon at its distal end coaxial with the exterior of the sheath; said sheath being divided internally into three lumens including an inflation lumen for admitting an inflation fluid into the balloon,
a flushing lumen with the sheath for conducting a flushing liquid to an orifice at the distal end of the catheter, and
an optical lumen; and
an optical assembly positioned in and directly and permanently bonded to the interior of said optical lumen without a separate supporting tube for the assembly, said assembly including a plurality of individual optical fibers formed of an optical quality, transparent plastic for transmitting light from the proximal end of the catheter, through the optical lumen, to the distal end of the catheter, thereby illuminating an object to be viewed, a bundle of optical fibers for transmitting an image of the illuminated object from the distal end of the catheter, through the optical lumen, to the proximal end of the catheter, and a gradient index objective lens bonded to the distal end of the fiber bundle and positioned within the optical lumen.

2. The catheter of claim 1, wherein said fiber bundle includes a plurality of pixels made of fused silica glass doped with a first dopant that increased the index of refraction of the silica glass, cladding for binding the pixels together formed form a glass doped with a second dopant that decreases the index of a refraction of the glass, and an opaque coating around the exterior of the imaging fiber bundle.

3. The catheter of claim 2, wherein the first dopant consist essentially of germanium dioxide, and the second dopant consist essentially of fluorene.

4. The catheter of claim 2, wherein the opaque coating consists essentially of an ultraviolet-cured epoxy.

5. The catheter of claim 1, including a guide wire removably positioned in said flushing lumen.

6. The catheter of claim 1, wherein the exterior diameter of said sheath is about 1.5 mm.

7. The catheter of claim 1, wherein said bundle comprises 2000 to 3000 individual optical fibers formed from a fused silica glass bound together by a cladding of glass, said individual fibers being approximately three or four microns in diameter.

8. The catheter of claim 7, including an opaque coating around the exterior of the bundle.

* * * * *